(12) United States Patent
Patel

(10) Patent No.: US 9,882,986 B2
(45) Date of Patent: *Jan. 30, 2018

(54) APPARATUS FOR CAPTURING BRUSHING HABITS

(71) Applicant: Ashtel Studios, Inc., Fontana, CA (US)

(72) Inventor: Anish Patel, Fontana, CA (US)

( * ) Notice: Subject to any disclaimer, the term of this patent is extended or adjusted under 35 U.S.C. 154(b) by 552 days.

This patent is subject to a terminal disclaimer.

(21) Appl. No.: 13/757,763

(22) Filed: Feb. 2, 2013

(65) Prior Publication Data

US 2013/0151662 A1    Jun. 13, 2013

Related U.S. Application Data

(63) Continuation of application No. 13/746,535, filed on Jan. 22, 2013.

(51) Int. Cl.
| | |
|---|---|
| G06F 19/00 | (2011.01) |
| H04L 29/08 | (2006.01) |
| G06F 17/30 | (2006.01) |
| A46B 15/00 | (2006.01) |

(52) U.S. Cl.
CPC .......... *H04L 67/12* (2013.01); *A46B 15/0004* (2013.01); *G06F 17/30386* (2013.01); *G06F 19/3418* (2013.01); *G06F 19/36* (2013.01); *A46B 15/0008* (2013.01); *A46B 2200/1066* (2013.01)

(58) Field of Classification Search
CPC ....... H04L 67/12; H04L 67/125; G06Q 50/22; G06F 19/34; G06F 19/3418; G06F 19/3431; G06F 19/36
See application file for complete search history.

(56) References Cited

U.S. PATENT DOCUMENTS

| | | |
|---|---|---|
| 6,536,068 B1 | 3/2003 | Yang et al. |
| 6,850,167 B2 | 2/2005 | Rosen |
| 6,923,409 B2 | 8/2005 | Strunk |
| 8,065,164 B2 | 11/2011 | Hwang |
| 8,075,315 B2 | 12/2011 | Gatzemeyer et al. |
| 8,137,109 B2 | 3/2012 | Gatzemeyer et al. |
| 8,201,295 B2 | 6/2012 | Gatzemeyer et al. |
| 8,533,892 B2 | 9/2013 | Dabrowski |
| 8,544,132 B2 | 10/2013 | Gatzemeyer et al. |
| 8,681,008 B2 | 3/2014 | Jimenez et al. |
| 8,758,022 B2 | 6/2014 | Kim |
| 8,789,227 B2 | 7/2014 | Cook et al. |
| 8,863,343 B2 | 10/2014 | Iwahori |
| 9,332,829 B2 | 5/2016 | Wu et al. |
| 2006/0123570 A1 | 6/2006 | Pace et al. |

(Continued)

FOREIGN PATENT DOCUMENTS

WO    2009154628 A    12/2009

OTHER PUBLICATIONS

Beam, "Beam Toothbrush Features", http://www.beamtoothbrush.com/beam/features.php, Jan. 21, 2013.

(Continued)

*Primary Examiner* — Aaron Strange
(74) *Attorney, Agent, or Firm* — LeonardPatel PC

(57) ABSTRACT

An apparatus that monitors the brushing history of a user is provided. In one embodiment, the apparatus, such as a toothbrush, may capture brushing data when a user is brushing teeth, and store the captured brushing data in a database of the apparatus.

9 Claims, 21 Drawing Sheets

(56) References Cited

U.S. PATENT DOCUMENTS

| | | | | |
|---|---|---|---|---|
| 2007/0136964 | A1* | 6/2007 | Dawley | A61C 17/221 15/22.1 |
| 2008/0109973 | A1* | 5/2008 | Farrell | A46B 7/04 15/4 |
| 2008/0256445 | A1* | 10/2008 | Olch | G06F 19/3418 715/700 |
| 2009/0092955 | A1* | 4/2009 | Hwang | A46B 15/0002 434/263 |
| 2009/0307859 | A1 | 12/2009 | Mottram et al. | |
| 2009/0317770 | A1* | 12/2009 | Gatzemeyer | A46B 15/0002 433/215 |
| 2010/0015589 | A1* | 1/2010 | Lehavi | G09B 23/283 434/263 |
| 2010/0281636 | A1* | 11/2010 | Ortins | A46B 9/04 15/4 |
| 2011/0146016 | A1* | 6/2011 | Gatzemeyer | A46B 13/023 15/167.1 |
| 2011/0275424 | A1* | 11/2011 | Schmid | A46B 15/0002 463/1 |

OTHER PUBLICATIONS

Nam V. Nguyen, "Notice of Allowance", dated Sep. 16, 2016 for U.S. Appl. No. 14/040,547.
Stephanie R. Berry, "Non-Final Office Action" dated Sep. 9, 2016 for U.S. Appl. No. 13/746,535.
Stephanie R. Berry, "Final Office Action" dated Mar. 10, 2016 for U.S. Appl. No. 13/746,535.
Stephanie R. Berry, "Non-final Office Action" issued in U.S. Appl. No. 13/746,535 dated Sep. 18, 2015.
Nam V. Nguyen, "Final Office Action" dated May 24, 2016 for U.S. Appl. No. 14/040,547.
Stephanie R. Berry, "Final Office Action", dated Apr. 6, 2017 for U.S. Appl. No. 13/746,535.
Nam V. Nguyen, "Non-Final Office Action" dated Jan. 7, 2016 for U.S. Appl. No. 14/040,547.
Stephanie R. Berry, "Non-Final Office Action", dated Oct. 4, 2017, U.S. Appl. No. 13/746,535.

* cited by examiner

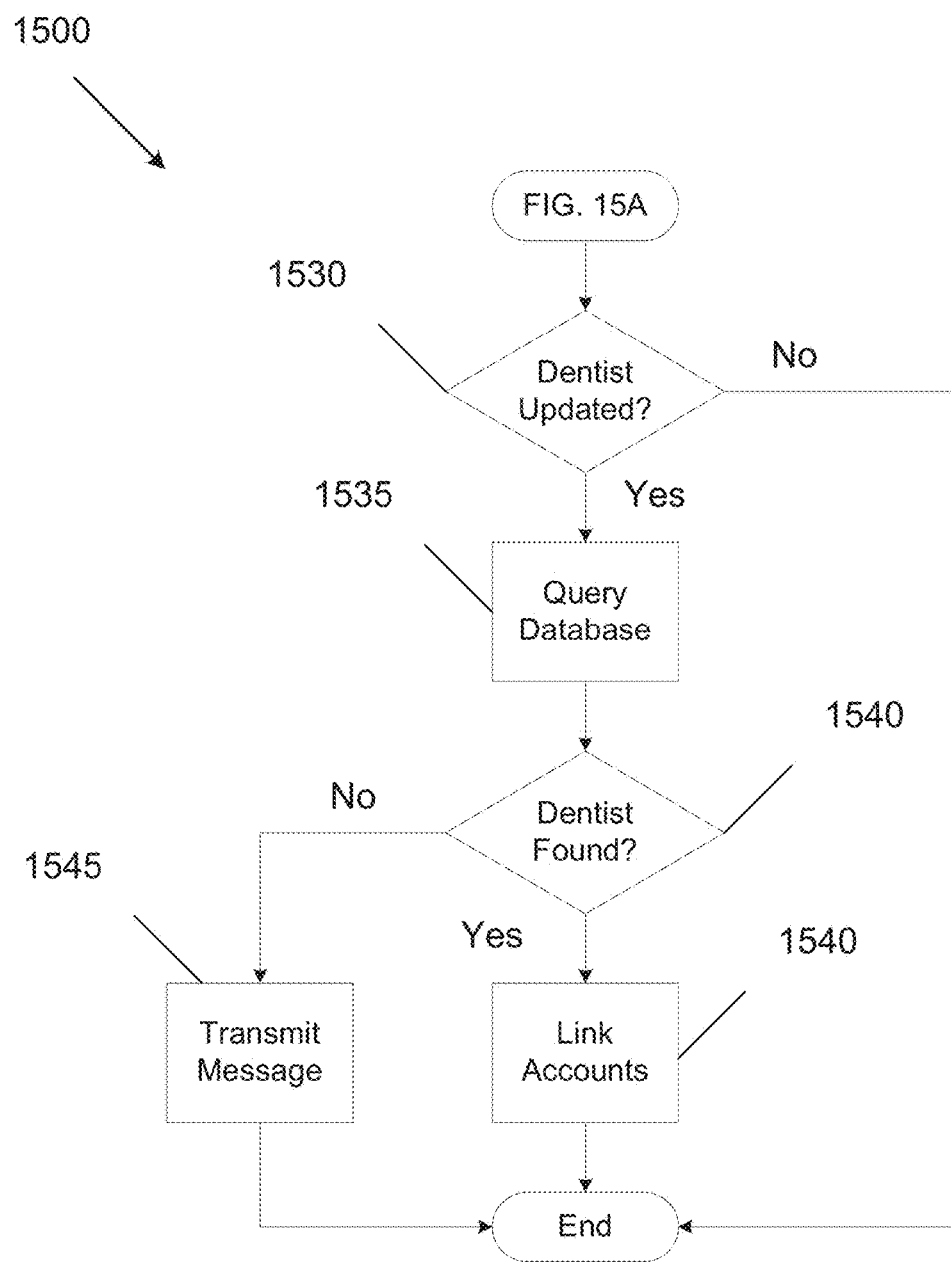

1700

APPARATUS FOR CAPTURING BRUSHING HABITS

CROSS-REFERENCE TO RELATED APPLICATION

This application is a continuation, and claims the benefit, of U.S. Non-Provisional patent application Ser. No. 13/746,535, filed on Jan. 22, 2013. The subject matter thereof is hereby incorporated herein by reference in its entirety.

FIELD

The present invention relates to brushing habits and, more particularly, to capturing brushing habits of a user of a toothbrush.

BACKGROUND

Generally, when a user brushes his or her teeth, the user is not able to determine his or her brushing habits. Also, professionals, such as dentists, or oral hygienist, etc., are not currently able to verify whether the user of the toothbrush is brushing his or her teeth according to the recommendations of the professional or the recommendations from the American Dental Association®. Accordingly, a toothbrush that captures brushing habits of the user may be beneficial.

SUMMARY

Certain embodiments of the present invention may provide solutions to the problems and needs in the art that have not yet been fully identified, appreciated, or solved by current toothbrushes. For example, some embodiments described herein allow a toothbrush to capture the brushing habits of a user.

In one embodiment, a method is provided. The method includes capturing, by a toothbrush, brushing data when a user is brushing teeth. The computer-implemented method also includes transmitting, by the toothbrush, the captured brushing data to a remote server.

In another embodiment, a computer-implemented method is provided. The computer-implemented method includes receiving, at a remote server, brushing data of a user from a toothbrush. The method also includes storing the brushing habits of the user in the toothbrush.

In yet another embodiment, an apparatus is provided. The apparatus includes at least one processor and memory that includes a computer program. The computer program, together with the processor, are configured to cause the apparatus to capture, via sensors, brushing data when a user is brushing teeth, and store the captured brushing data in a database.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIGS. 15A and 15B are flow diagrams illustrating a process for linking a professional when a new user profile is created or modified, according to an embodiment of the present invention.

DETAILED DESCRIPTION OF THE EMBODIMENTS

Some embodiments of the present invention pertain to capturing brushing habits of a user when the user is brushing his or her teeth. In one embodiment, a sensor is activated prior to the user brushing his or her teeth, and the sensor is configured to capture brushing data while the user brushes his or her teeth. Upon completion of data capture, the brushing data may be stored in a database of the toothbrush and/or transmitted to a remote server for storage in an external database and viewing by the user or a user-approved professional.

Figure 1A:
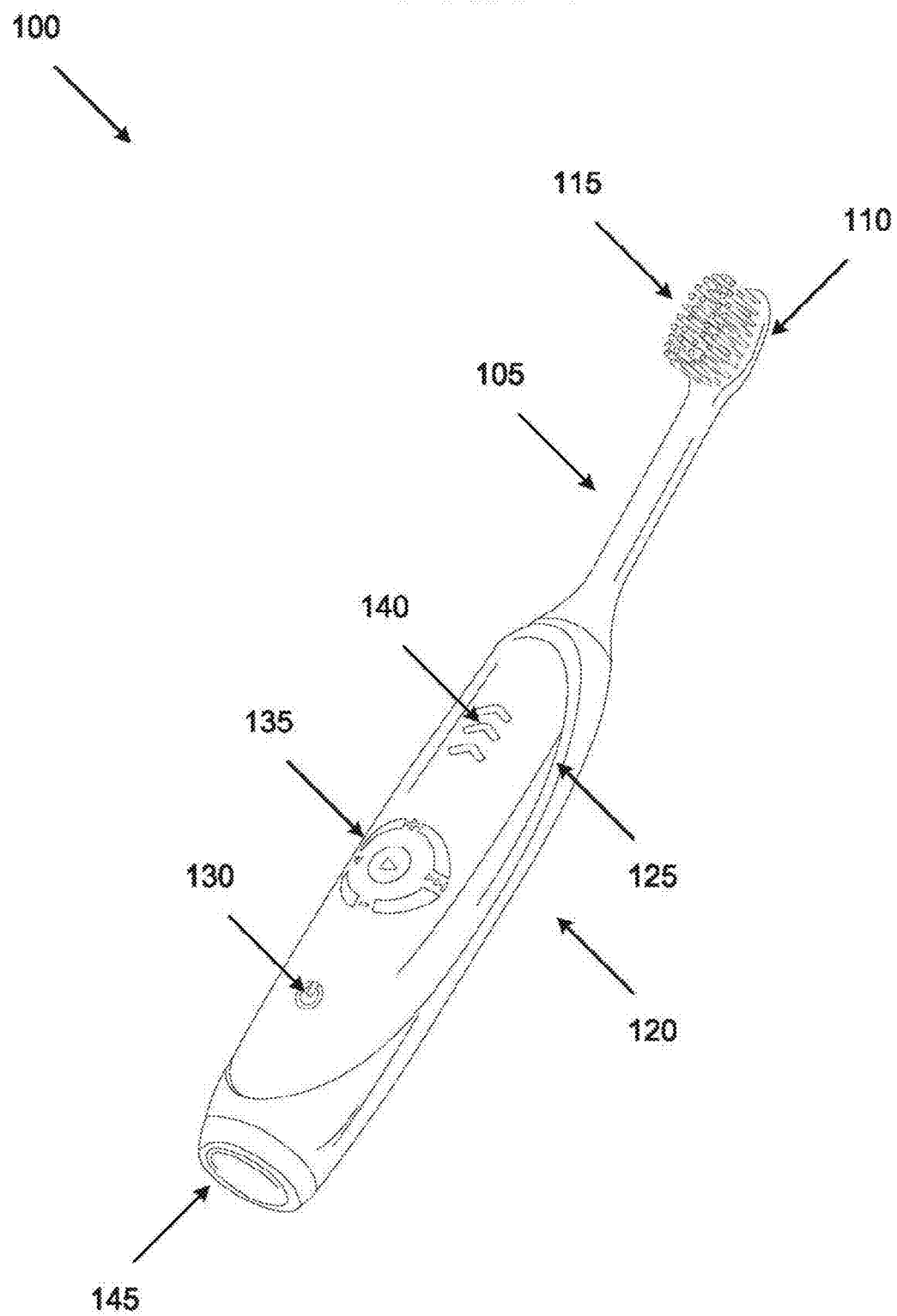
FIGS. 1A and 1B illustrate perspective views of a toothbrush, according to an embodiment of the present invention.
Figure 1B:
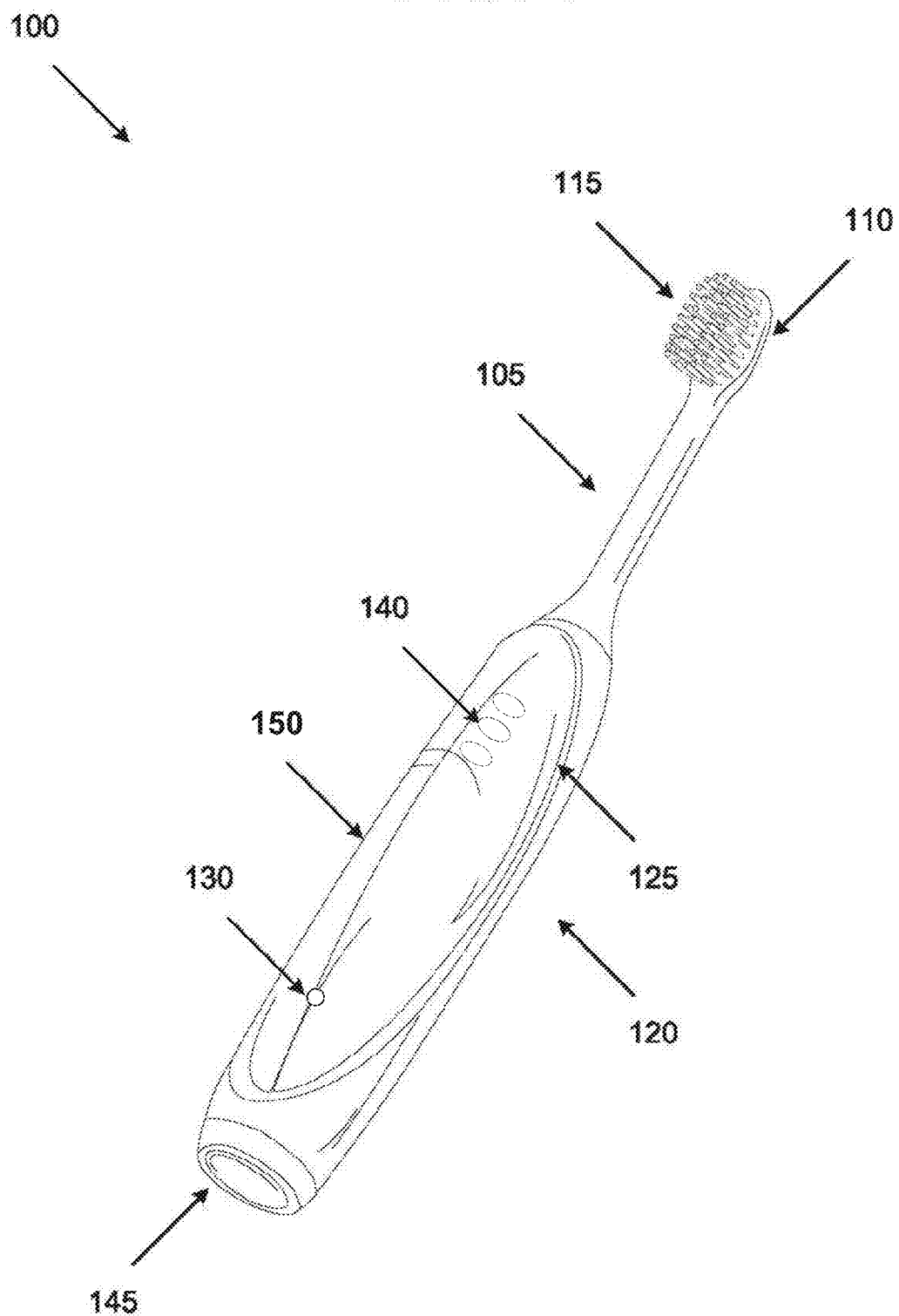

FIGS. 1A and 1B illustrate perspective views of a toothbrush 100, according to an embodiment of the present invention. Toothbrush 100 may include an elongated segment 105, a body segment 120, and an end segment 145. Elongated segment 105 may attach to and detach from body segment 120. Body segment 120 may include a locking mechanism (not shown) in order for elongated segment 105 to attach to and detach from body segment 120.

Body segment 120 may also include a removable cover 125. Removable cover 125 may include a power on and off switch (hereinafter "switch") 130, a selection unit 135, and a mode identification unit 140. Switch 130 may be configured to power toothbrush 100 on and off. Selection unit 135 may be configured to select a mode of operation (e.g., sensitive mode, deep clean mode, etc.), select a radio station, select music from a playlist, etc. Mode identification unit 140 may identify the mode of operation. Any combination of modes and features are possible in some embodiments.

In some embodiments, removable cover 125 may include a liquid crystal display (LCD) panel 150 with a switch 130 configured to power toothbrush 100 on and off. LCD 150 may also show the mode of operation via mode identification unit 140.

Removable cover 125 may be detached from body segment 120. This may allow a user to replace batteries when necessary. End segment 145 may be attached to body segment 120, and may include a plurality of slits or holes that facilitate transmission of sound to enable a user to listen to selected digital media or to a radio station.

Figure 2:
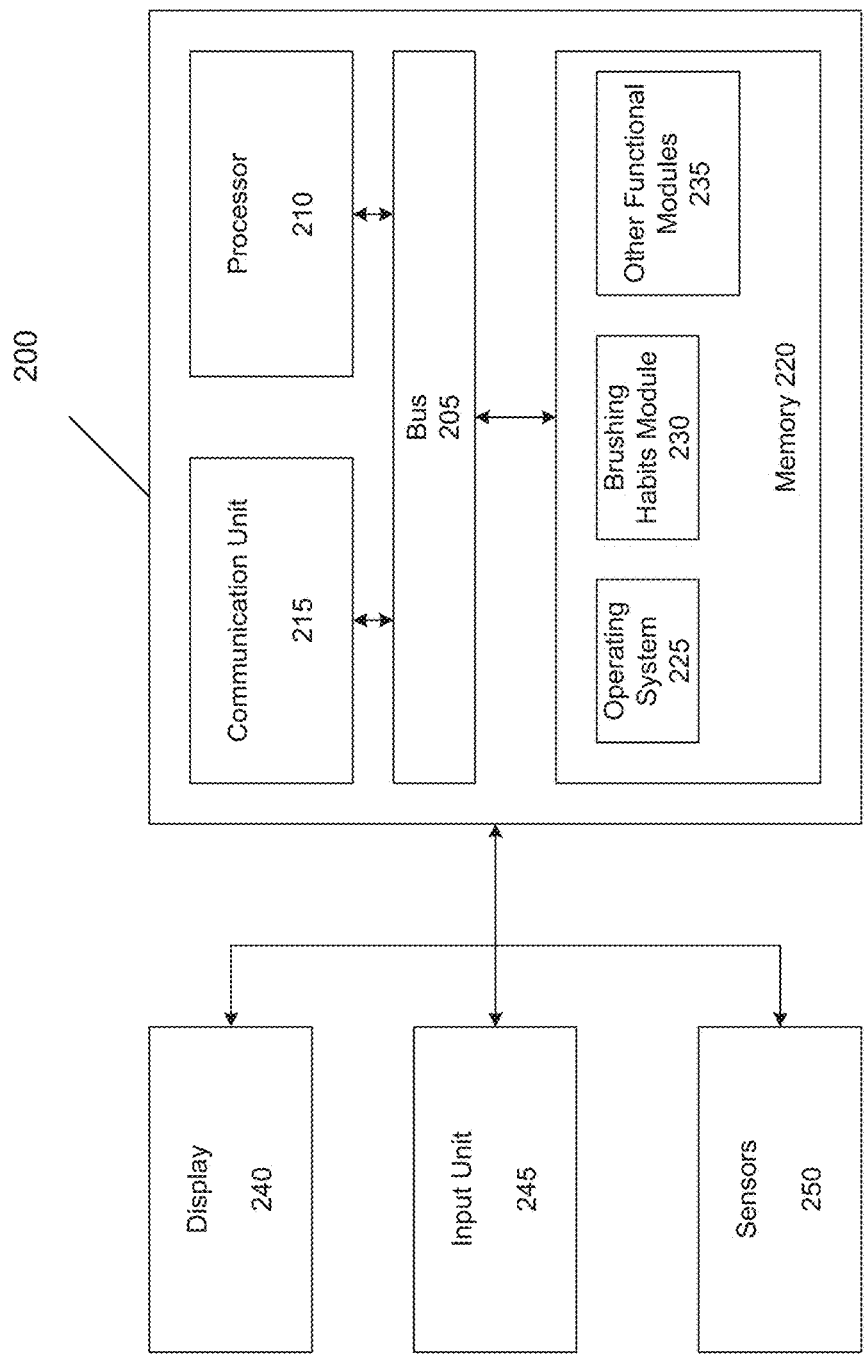
FIG. 2 is a block diagram illustrating a system, according to an embodiment of the present invention.

FIG. 2 is a block diagram illustrating a computing system 200 of the toothbrush, according to an embodiment of the present invention. System 200 may include a bus 205 or other communication mechanism that can communicate information and a processor 210, coupled to bus 205, that can process information. Processor 210 can be any type of general or specific purpose processor. System 200 may also include memory 220 that can store information and instructions to be executed by processor 210. Memory 220 may include any combination of random access memory ("RAM"), read only memory ("ROM"), static storage such as a magnetic or optical disk, or any other type of computer readable medium. System 200 may also include a communication device 215, such as a network interface card, that may provide access to a network. In certain embodiments, a universal serial bus (not shown) may connect to, and communicate with, system 200.

The computer readable medium may be any available media that can be accessed by processor 210. The computer readable medium may include both volatile and nonvolatile medium, removable and non-removable media, and communication media. The communication media may include computer readable instructions, data structures, program modules, or other data and may include any information delivery media.

Processor 210 can also be coupled via bus 205 to a display 240, such as a Liquid Crystal Display ("LCD"). Display 240 may display a variety of information to the user, such as timing information related to brushing teeth, professional recommendation information, brushing data, toothbrush settings, a radio channel, brush head quality, or any other information that would be appreciated by a person of ordinary skill in the art. In some embodiments, a haptic (i.e., touch) control interface may be integrated into display 240 and/or included as part of a separate haptic sensing system. An input unit 245, such as one or more buttons, may also be coupled to bus 205 to enable the user to interface with system 200. Also coupled to bus 205 may be sensors 250 located in the head of the brush. Sensors 250, as will be described in more detail below, may collect data related to brushing motion, pressure applied to teeth when brushing, quadrants/areas brushed, etc.

According to one embodiment, memory 220 may store software modules that may provide functionality when executed by processor 210. The modules can include an operating system 225 and a brushing habits module 230 configured to record brushing habits, as well as other functional modules 235. Operating system 225 may provide operating system functionality for system 200. Brushing habits module 230 may cause sensors 250 to collect data, and may retrieve data collected from sensors 250, and periodically, and/or when instructed, transmit the data to a remote server and/or directly to a professional for evaluation. Because system 200 may be part of a larger system, system 200 may include one or more additional functional modules 235 to include the additional functionality.

For example, additional functional modules 235 may include a user setup module. The user setup module may allow the user to configure the toothbrush prior to operating the toothbrush. For example, the user may create a user profile, enter the date the user last visited the professional, select the type of bristles used (e.g., soft bristles, medium bristles, hard bristles, etc.), select the type of toothpaste used, etc. The user may also indicate whether he or she has, for example, various dental conditions such as sensitive teeth or cavities. It should be appreciated that a computing device may allow the user create the user profile and configure the toothbrush settings by accessing a website on a remote server, and transmit the toothbrush setup data to the toothbrush via a Wi-Fi connection, a Bluetooth® connection, or via any wired or wireless communication means that would be appreciated by a person of ordinary skill in the art. In some embodiments, a professional may configure the toothbrush for the user.

Once the toothbrush is configured in this embodiment, the user may begin using the toothbrush. For example, each time the user brushes his or her teeth, sensors 250 may capture data and store the captured data in memory 220. The captured data may include, but is not limited to, the amount of pressure applied to a user's teeth when brushing, the duration of brushing, the quadrants/areas that were brushed, the direction or rotation of the toothbrush movement, the time spent brushing in each quadrant, and/or any other data that would help evaluate the brushing habits of the user.

Brushing habits module 230 may transmit the captured data to a remote server via communication unit 210. For example, the captured data may be transmitted via Wi-Fi, a Universal Serial Bus ("USB") connection, Bluetooth®, or via any suitable wired or wireless communication means. In another embodiment, brushing habits module 230 may transmit the captured data to a pre-authorized professional. It should be appreciated that the transmission of data may occur once a day, once a week, once a month, or after any preconfigured time period. It should be appreciated that the user may modify when the captured data should be transmitted, and/or may choose to transmit the data at a certain time manually.

Although not illustrated in FIG. 2, a power supply and a power on/off switch may also be connected to system 200 of the toothbrush. The power supply may be a rechargeable power supply, and may use AA batteries, AAA batteries, lithium ion batteries, or any type of battery sufficient to power the toothbrush. The power on/off switch may allow system 200 to power the toothbrush on or off depending on the state of the toothbrush.

Figure 3:
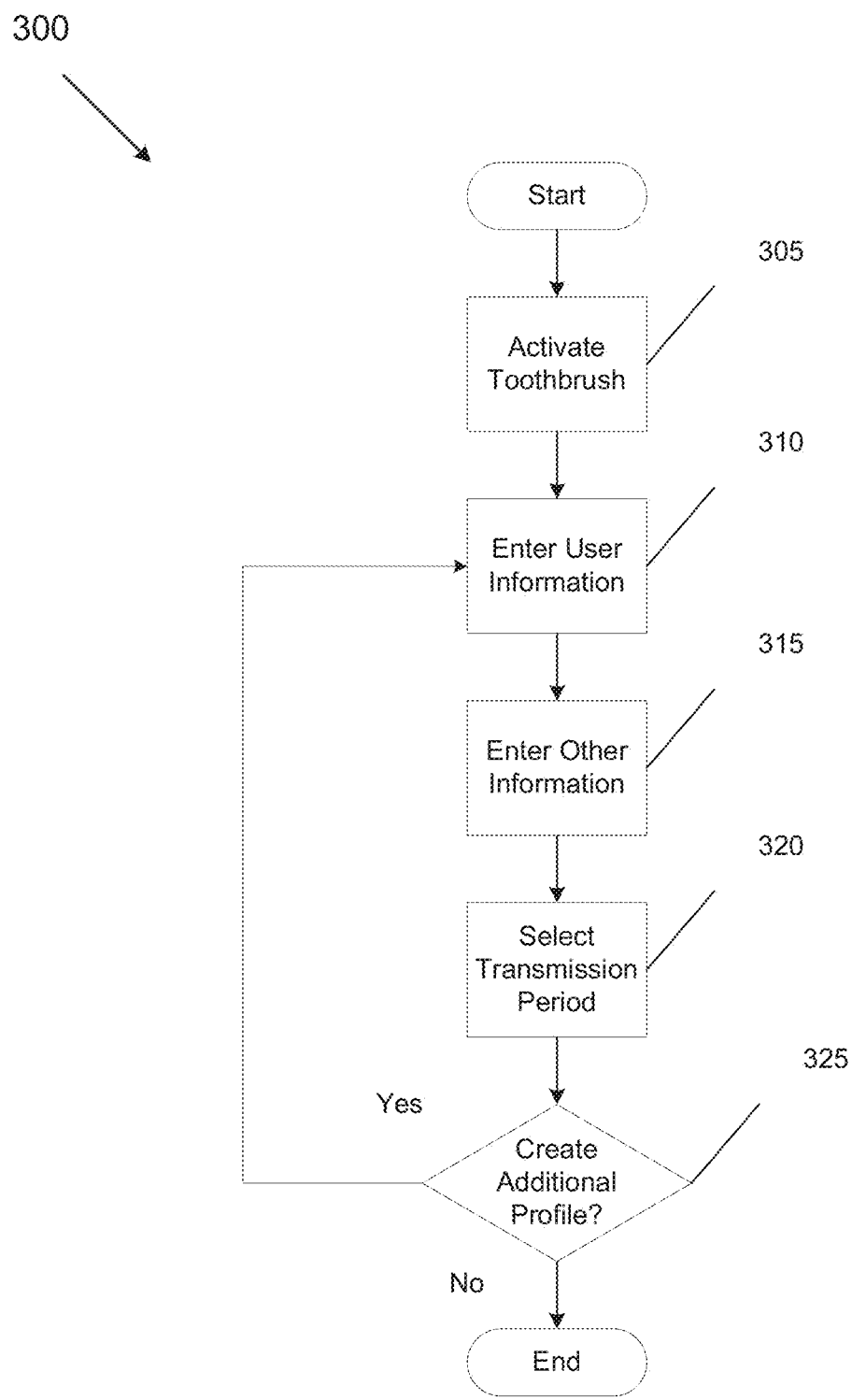
FIG. 3 is a flow diagram illustrating a process for registering a user of a toothbrush, according to an embodiment of the present invention.

FIG. 3 is a flow diagram illustrating a process 300 for registering a user of a toothbrush, according to an embodiment of the present invention. The system shown in FIG. 2 may be configured to execute process 300 of FIG. 3 in some embodiments. Process 300 begins with the user at 305 activating the toothbrush. At 310, the user may enter user information to create a user profile. The user information may include, but is not limited to, name, age, sex, etc. At 315, the user may enter other information, such as the type of bristles, the toothpaste type, whether the user has sensitive teeth, the date of the previous professional visit, and any other information that would be appreciated by a person of ordinary skill in the art. At 320, the user may select a time period to transmit data related to user brushing habits. The time period may be once a day, once a week, every time the brush is utilized, or any other time period that would be appreciated by a person of ordinary skill in the art. In some embodiments, the user may select a default setting for transmission of data. At 325, the system determines whether additional user profiles should be created. If additional user profiles should be created, process 300 returns to 310 to allow the user to enter user information to create another user profile. If additional user profiles should not be created, process 300 terminates and the user may then begin using the toothbrush.

Figure 4:
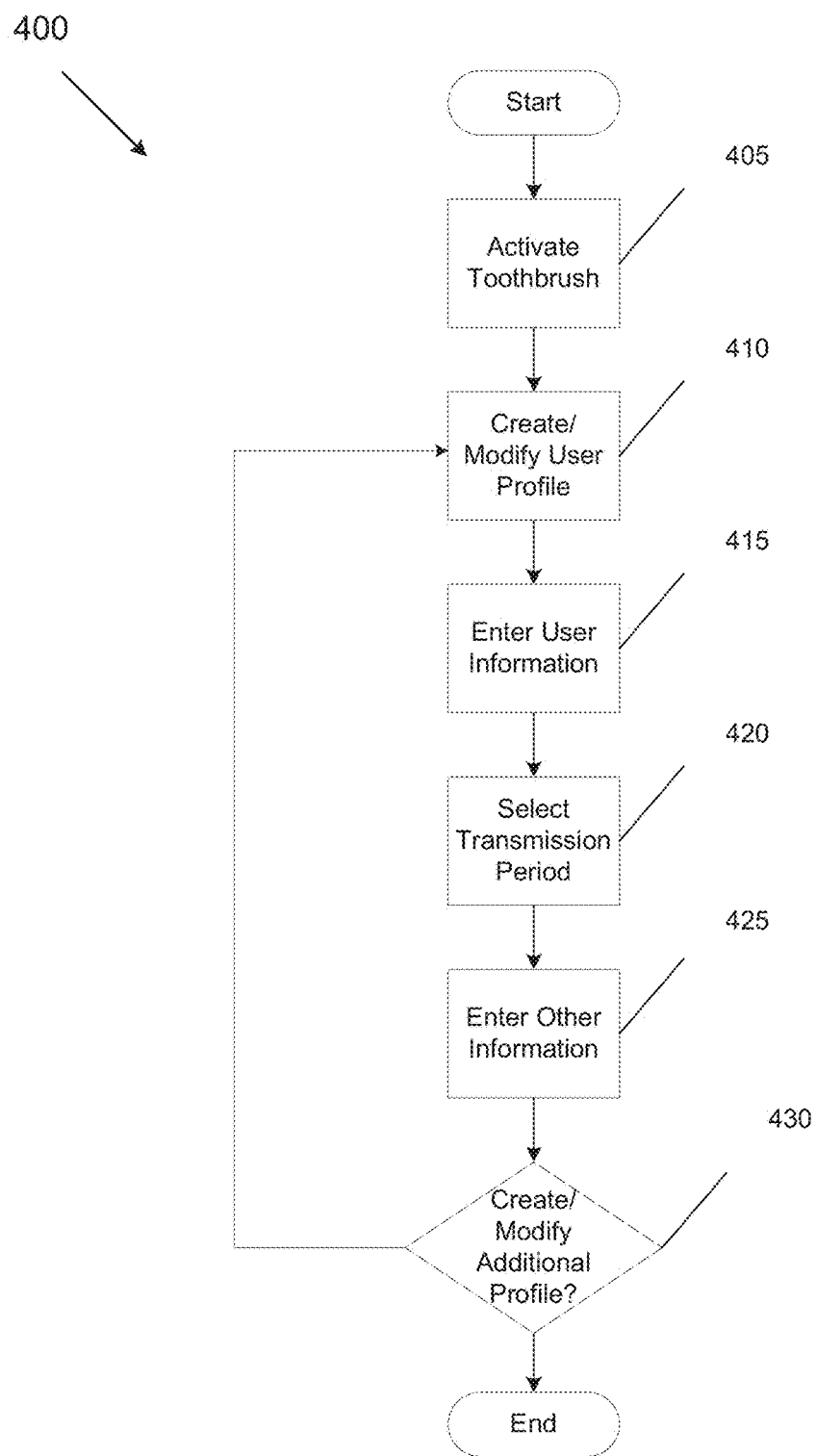
FIG. 4 is a flow diagram illustrating a process for modifying a user profile, according to an embodiment of the present invention.

FIG. 4 is a flow diagram illustrating a process 400 for modifying a user profile, according to an embodiment of the present invention. Process 400 begins with the user activating the toothbrush at 405. The toothbrush may be activated when the user presses the power on/off switch. If the toothbrush includes a sleep mode, the toothbrush may activate (or wake up) from sleep mode when any button is pressed on the toothbrush.

At 410, the user may select an option from a list of options to modify an existing user profile or create a new user profile. At 415, the user may enter user information, and, at 420, the user may enter other information such as the type of bristles, the toothpaste type, whether the user has sensitive teeth, the date of the previous professional visit, and any other information that would be appreciated by a person of ordinary skill in the art. At 425, the user may select a time period to transmit data related to user brushing habits. At 430, the system determines whether additional user profiles should be created. If additional user profiles should be created, process 400 returns to 410 to allow the user to enter user information to create another user profile. If additional user profiles should not be created, process 400 terminates and the user may then begin using the toothbrush.

Figure 5:
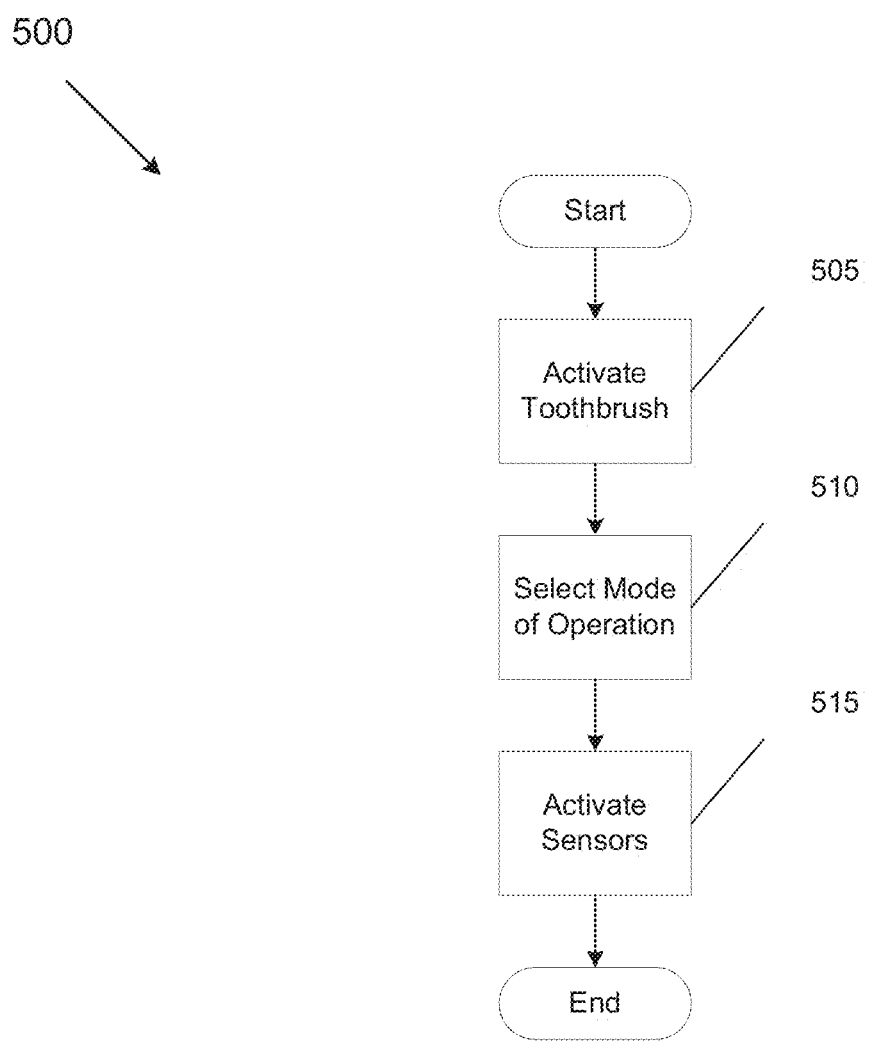
FIG. 5 is a flow diagram illustrating a process for activating brushing sensors, according to an embodiment of the present invention.

FIG. 5 is a flow diagram illustrating a process 500 for activating brushing sensors, according to an embodiment of the present invention. Process 500 begins with the user activating the toothbrush at 505. The toothbrush may be activated by pressing the power on/off switch. If the toothbrush includes a sleep mode, the toothbrush may activate (or wake up) from sleep mode when any button is pressed on the toothbrush.

At 510, the user may select a mode of operation on the toothbrush. For example, the mode of operation may include sensitive, deep clean, or any mode of operation that would be appreciated by a person of ordinary skill in the art. At 515, the brush sensors may be activated to allow brushing habits to be collected and stored in a memory of the toothbrush. In some embodiments, the brush sensors may include an activation delay to compensate for the time it takes the user to place the brush in his or her mouth and start brushing. The activation delay may be 3 seconds, 5 seconds, or any suitable time period. The toothbrush may include a preprogrammed activation delay or a user-customized delay. In certain embodiment, the toothbrush may also include a countdown timer, such that the user of the toothbrush can hear that the brush will activate in, for example, 3 second, 2 seconds, 1 second, etc. This may be heard via an audio device, or viewed via the LCD display, of the toothbrush.

Figure 6:
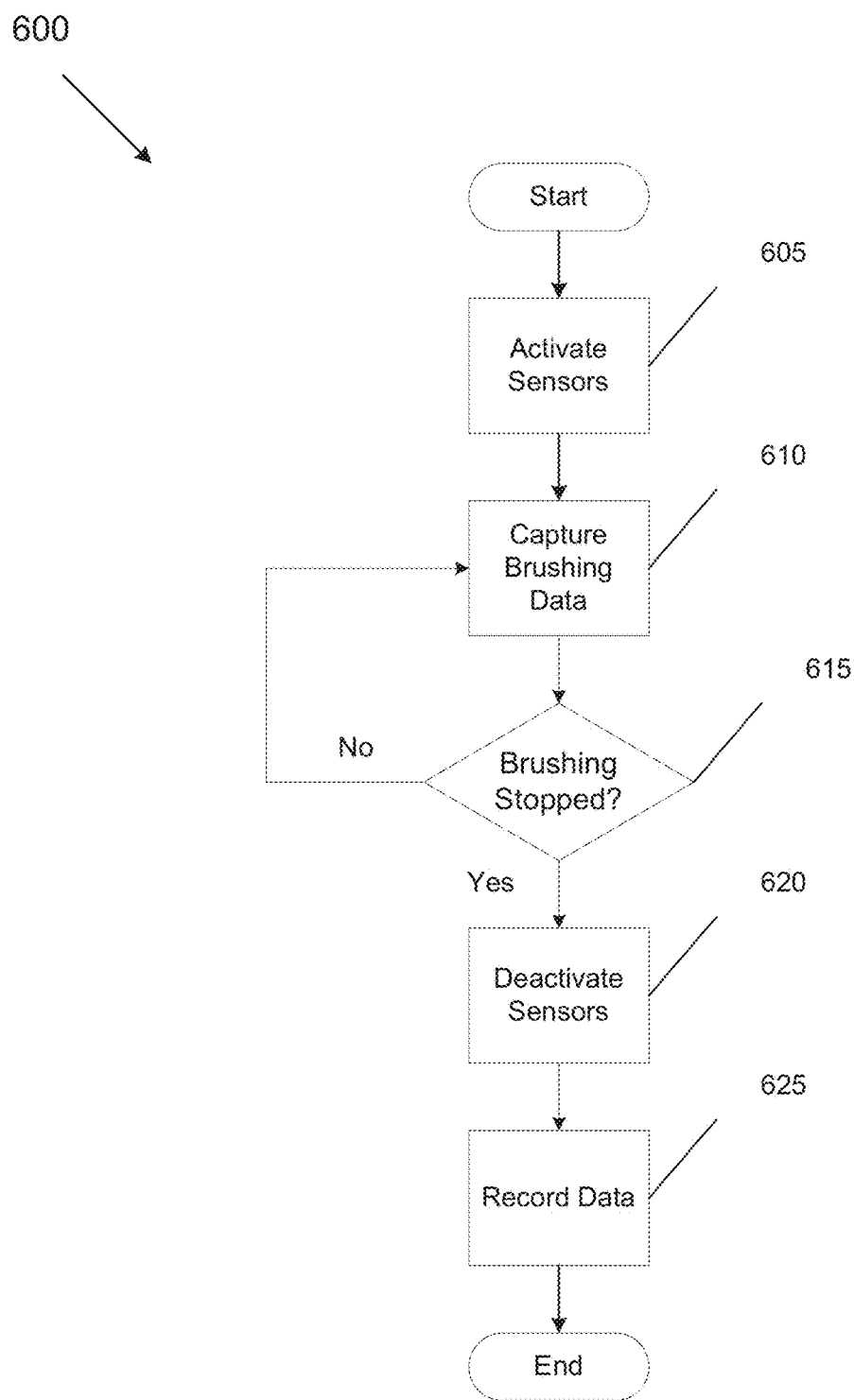
FIG. 6 is a flow diagram illustrating a process for capturing brushing data, according to an embodiment of the present invention.

FIG. 6 is a flow diagram illustrating a process 600 for capturing brushing data, according to an embodiment of the present invention. Process 600 begins with the toothbrush activating the brushing sensors after a predefined period of time at 605. At 610, the brushing sensors capture brushing data. The brushing sensors in this embodiment are active for a predefined period of time. The brushing sensors may transmit data periodically (for instance, once every tenth of a second), or may transmit data once a threshold of motion is exceeded and/or when a certain pattern of brushing is detected. The predefined period of time may be modified depending on the configuration of the toothbrush.

At 615, the toothbrush may determine whether the user has stopped brushing his or her teeth. If the user continues to brush his or her teeth during the predefined period of time, process 600 continues to capture the brushing data at 610. If the user discontinues brushing before the predefined period of time has elapsed or if the predefined period has elapsed prior to the user discontinuing brushing his or her teeth, the brushing sensors are deactivated at 620 and the brushing data is recorded in a database at 625. Data such as start time of brushing and stop time of brushing may also be recorded.

Figure 7:
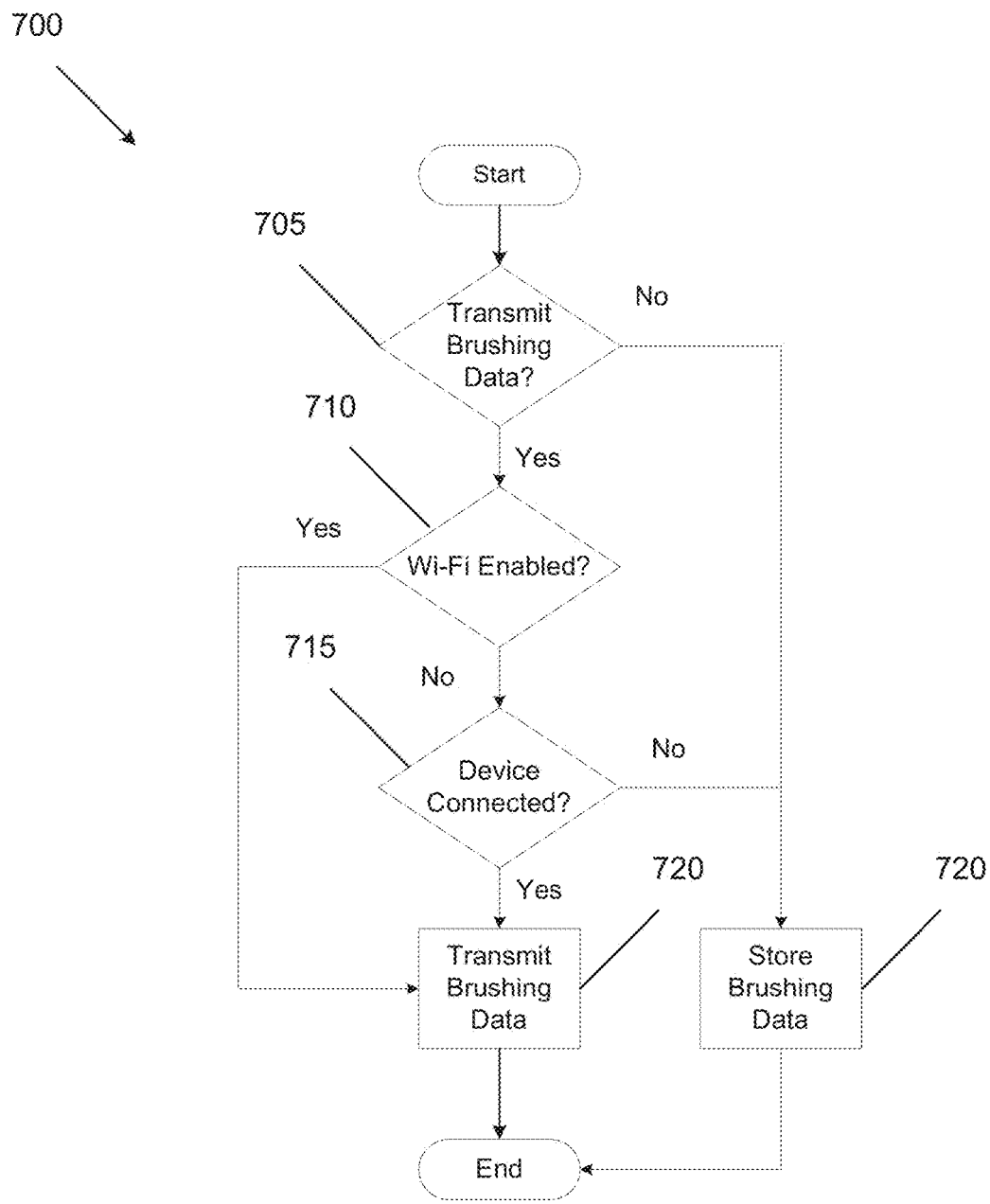
FIG. 7 is a flow diagram illustrating a process for transmitting brushing data, according to an embodiment of the present invention.

FIG. 7 is a flow diagram illustrating a process 700 for transmitting brushing data, according to an embodiment of the present invention. Process 700 begins at 705 with the toothbrush determining, at a predetermined time, whether to transmit data to a remote server or to any other computing device, such as a mobile device, a personal digital assistant, etc. In one embodiment, the toothbrush may be in a sleep (or standby) mode and may activate at predetermined periods of time to determine whether brushing data should be transmitted. In other embodiments, the toothbrush may perform such a determination each time brushing data is recorded, on a predetermined time interval (e.g., every week, every two weeks, every month, etc.), at the user's request, or at any time that would be appreciated by a person of ordinary skill in the art.

At 710, the toothbrush determines whether Wi-Fi is enabled/available. If Wi-Fi is enabled, the toothbrush transmits brushing data at 720 to a remote server or to any computing device that would be appreciated by a person of ordinary skill in the art. If Wi-Fi is not enabled/available, at 715, the toothbrush determines whether a device, such as a USB device, a computing device, etc., is connected to the toothbrush. If the toothbrush is connected to a device, the toothbrush transmits brushing data at 720 to a remote server or to any suitable computing device. If the toothbrush is not connected to any device, the toothbrush stores 725 the data until Wi-Fi connection is enabled/available or a wired connection is available so the brushing data can be transmitted at a later time. This may be particularly beneficial when, for example, a user of the toothbrush is on a trip or vacation and no wireless or wired connection is available.

It should be appreciated that, in certain embodiments, the brushing data may be deleted after each transmission. In other embodiments, the brushing data may be deleted after a predefined period of time, or when the user manually deletes the brushing data.

Figure 8:
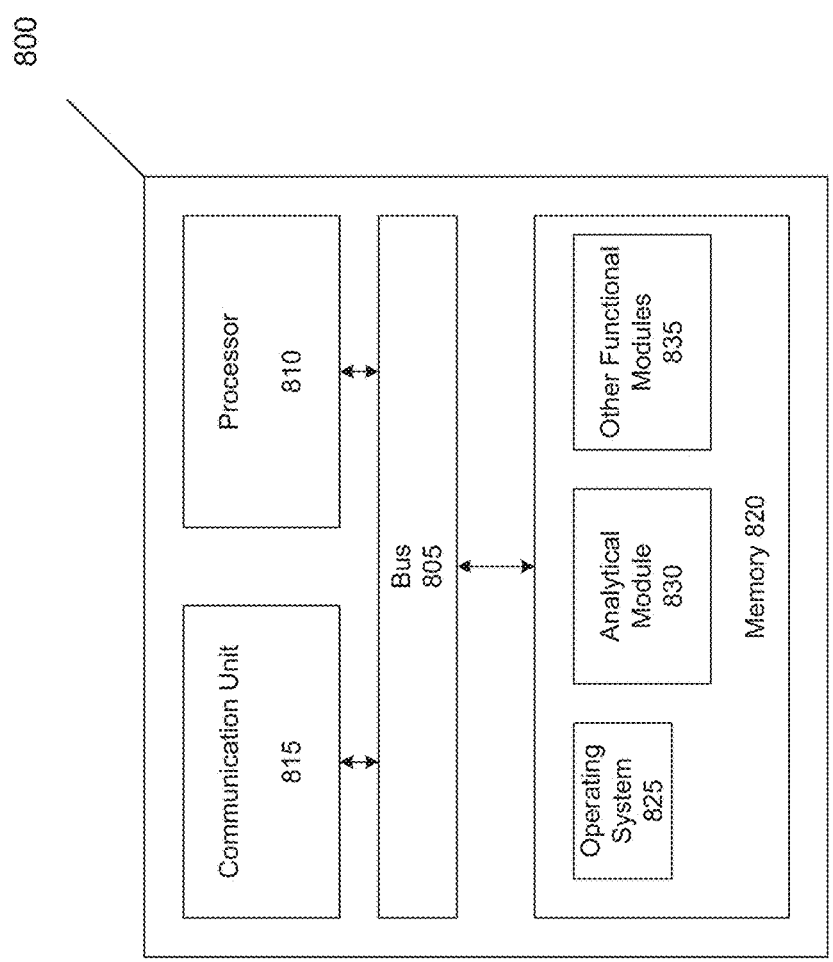
FIG. 8 is a block diagram of a remote server, according to an embodiment of the present invention.

FIG. 8 is a block diagram of a remote server 800, according to an embodiment of the present invention. Server 800 may include a bus 805 or other communication mechanism that can communicate information and a processor 810, coupled to bus 805, that can process information. Processor 810 can be any type of general or specific purpose processor. Server 800 may also include memory 820 that can store information and instructions to be executed by processor 810. Memory 820 may include any combination of random access memory ("RAM"), read only memory ("ROM"), static storage such as a magnetic or optical disk, or any other type of computer readable medium. Server 800 may also include a communication device 815 that may communicate with other devices, such as a toothbrush.

The computer readable medium may be any available medium that can be accessed by processor 810. The computer readable medium may include both volatile and non-volatile media, removable and non-removable media, and communication media. The communication media may include computer readable instructions, data structures, program modules, or other data and may include any information delivery media.

According to one embodiment, memory 820 may store software modules that may provide functionality when executed by processor 810. The modules can include an operating system 825 and an analytical module 830, as well as other functional modules 835. Operating system 825 may provide operating system functionality for system 800. Analytical module 830 may receive and store brushing data from a toothbrush. In certain embodiments, analytical module 830 may, for example, transmit the brushing data to a computing system of a user-authorized professional for evaluation, and/or may execute evaluation algorithms on the data to determine brushing habits. Because system 800 may be part of a larger system, system 800 may include one or more additional functional modules 835 to include the additional functionality.

Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration ("VLSI") circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Figure 9:
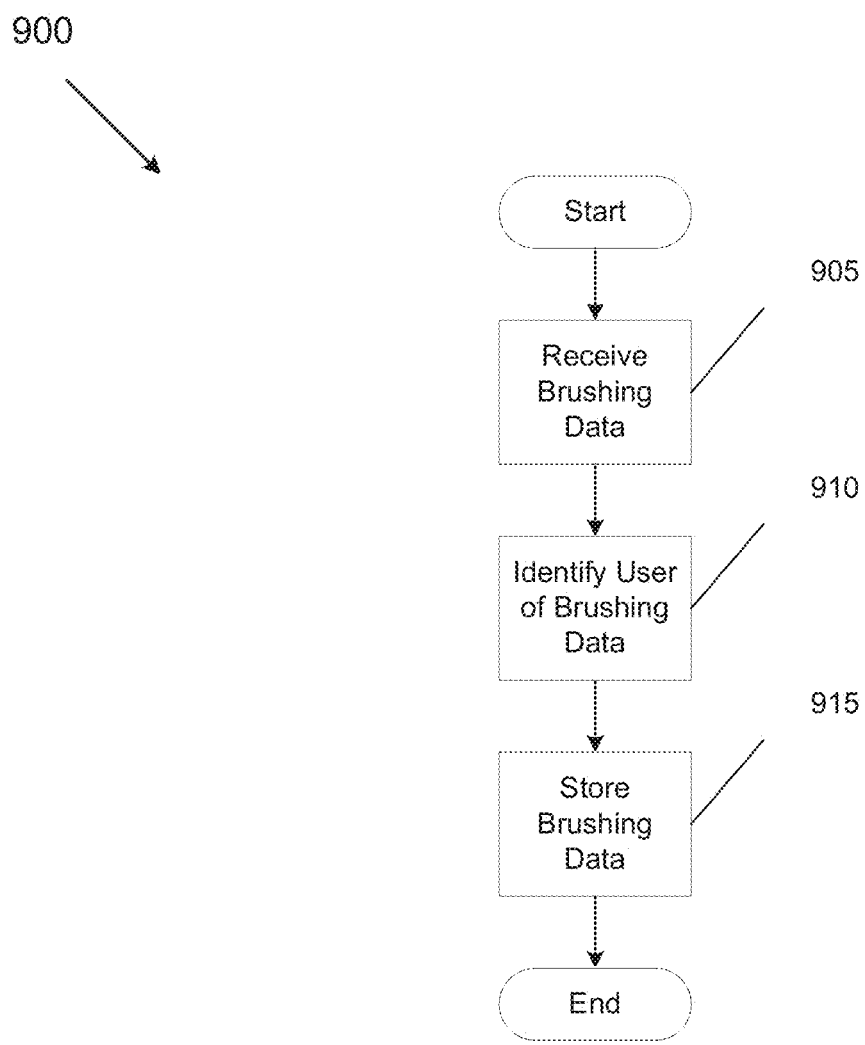
FIG. 9 is a flow diagram illustrating a process for receiving brushing data, according to an embodiment of the present invention.

FIG. 9 is a flow diagram illustrating a process 900 for receiving brushing data, according to an embodiment of the present invention. In some embodiments, process 900 may be executed by analytical module 830 of remote server 800. Process 900 begin with receiving brushing data from a registered toothbrush at 905. At 910, the remote server determines the user of the brushing data. For example, brushing data may include a toothbrush identification number each time data is received from a toothbrush to identify the user of the toothbrush. It should be noted that brushing data may include other identification data to identify the user of the toothbrush. At 915, the remote server stores in a database brushing data associated with the user of the toothbrush. This may allow the brushing data to be linked with the profile of the user.

Figure 10:
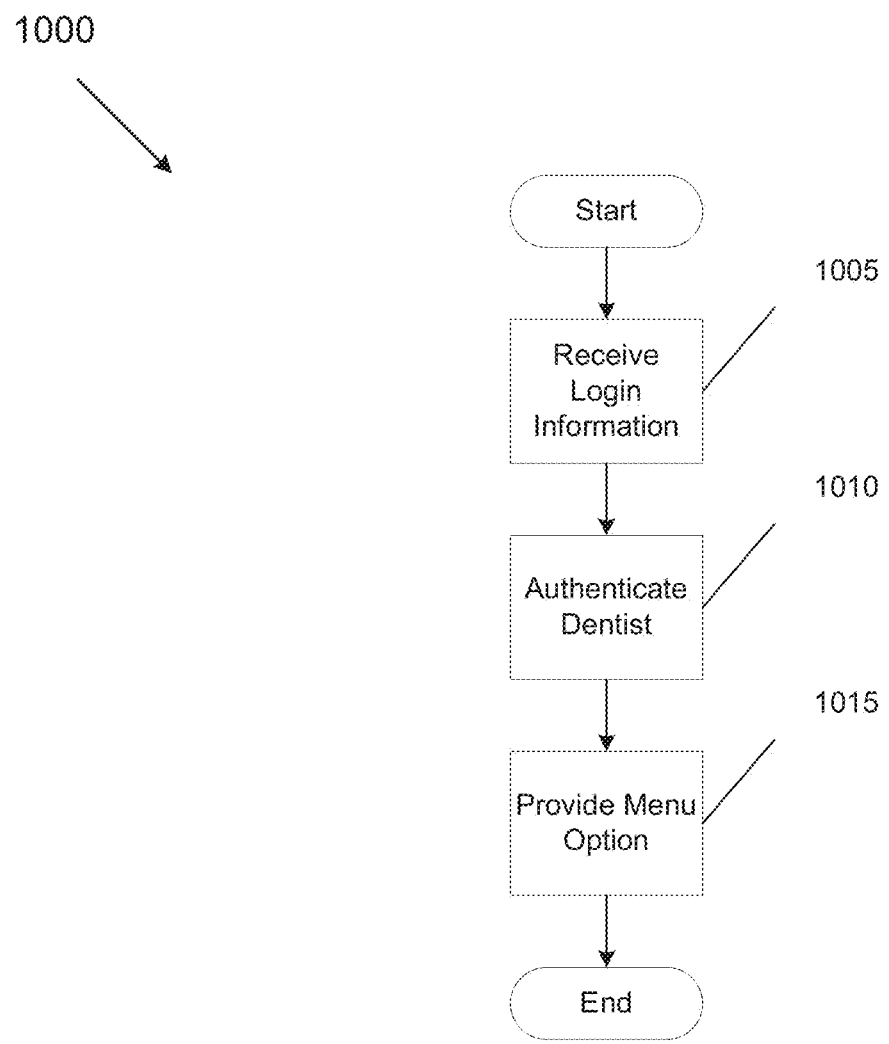
FIG. 10 is a flow diagram illustrating a process for providing access to a professional, according to an embodiment of the present invention.

FIG. 10 is a flow diagram illustrating a process 1000 for providing access to a professional, according to an embodiment of the present invention. In some embodiments, process 1000 may be executed by analytical module 830 of remote server 800. Process 1000 may begin with receiving login information (e.g., a user name and password) at 1005 from a computing system of a professional. At 1005, the remote server authenticates the professional, and provides the professional with a menu option at 1010. The menu option may include an option to view a list of patients associated with the professional, an option to add/remove/modify a patient, an option to modify the settings, etc.

Figure 11:
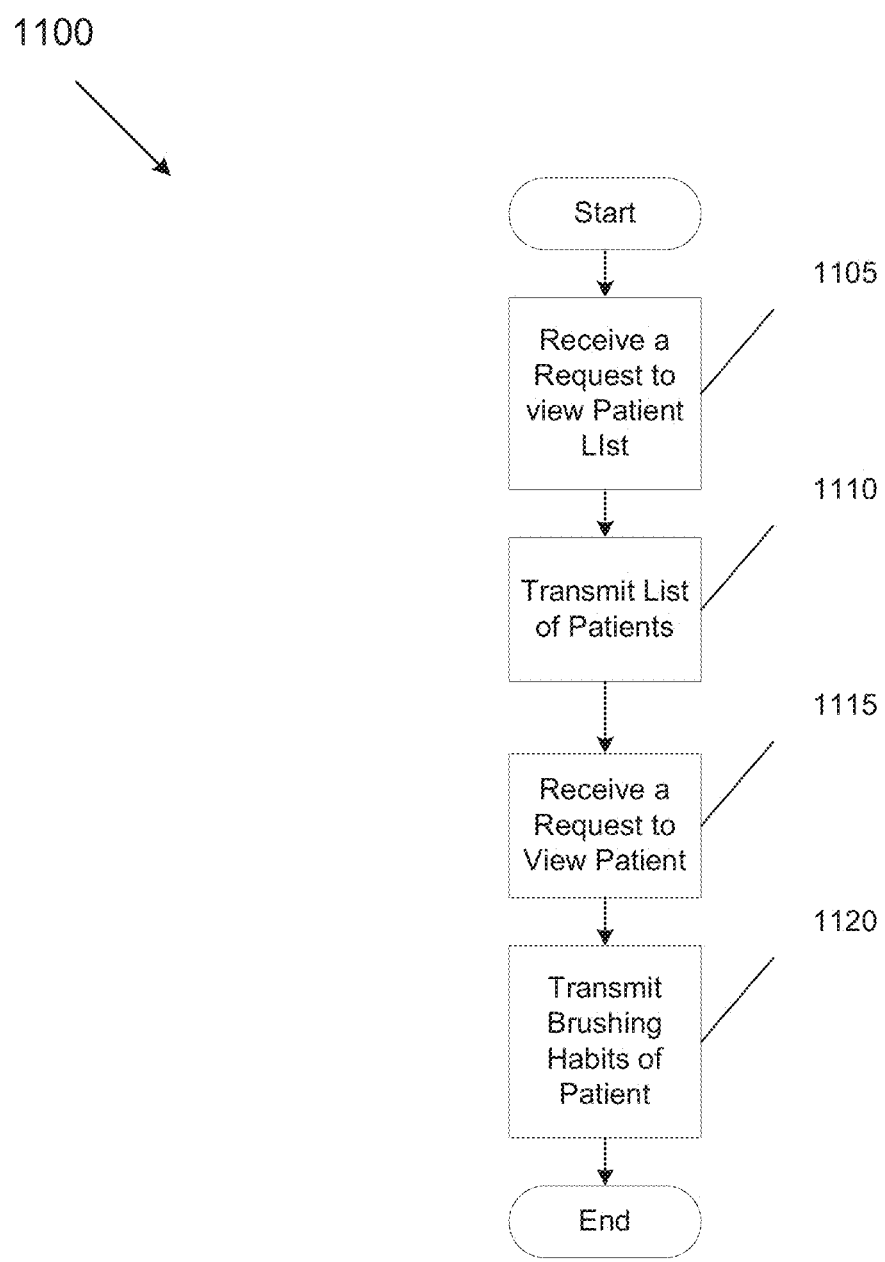
FIG. 11 is a flow diagram illustrating a process for providing a professional with brushing data associated with a user, according to an embodiment of the present invention.

FIG. 11 is a flow diagram illustrating a process 1100 for providing a professional with brushing data associated with a user, according to an embodiment of the present invention. In some embodiments, process 1100 may be executed by analytical module 830 of remote server 800. Process 1100 may begin with the remote server receiving a request at 1105 from a computing system of a professional to view a list of patients. In this embodiment, the list may be patients of the professional. At 1110, the remote server transmits the list of patients to the computing system of the professional.

At 1115, the remote server receives a selection from the computing system of the professional to view brushing habits of a particular patient or to provide updated instructions to the patient based on the brushing habits. At 1120, the remote server transmits brushing data to the computing system of the professional such that the professional can view the brushing habits of the patients over a predefined period of time.

Figure 12:
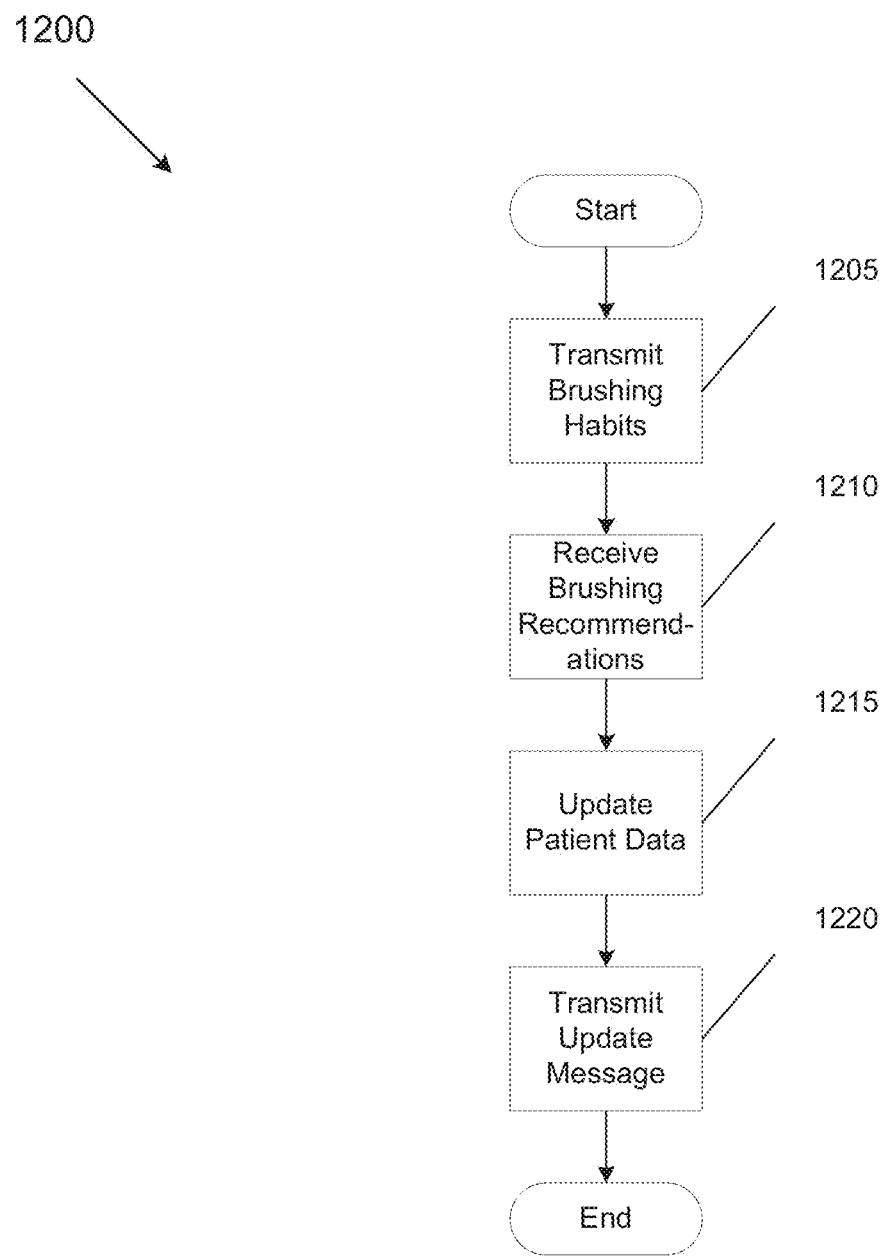
FIG. 12 is a flow diagram illustrating a process for receiving professional recommendations for a user of a toothbrush, according to an embodiment of the present invention.

FIG. 12 is a flow diagram illustrating a process 1200 for receiving professional recommendations for a user of a toothbrush, according to an embodiment of the present invention. In some embodiments, process 1200 may be executed by analytical module 830 of remote server 800.

Process 1200 may begin with the remote server transmitting brushing habits of the patient to the computing system of the professional at 1205.

By receiving the brushing habits of the patient, the professional may be able to view the patient's brushing habits. For example, the professional may view the usage of the toothbrush over a predefined period of time, record the patient's symptoms (e.g., date-wise), may compare patient's change in symptoms with the patient's toothbrush usage history, etc. Based on the brushing habits of the patient, the professional may make some recommendation in order for the patient to improve the health of his or her teeth. For example, at 1210, the remote server receives professional recommendation information from the computing system of the professional for the patient. At 1215, the remote server updates the patient's data to reflect the recommendations of the professional. In certain embodiments, the remote server may transmit an update message at 1220 to the toothbrush of the patient when professional recommendations are made to the patient's data. In some embodiments, the update message will be transmitted to a mobile device of the user, to an email account of the user, etc.

It should be appreciated that the update message (or recommendation information of the professional) may configure, reconfigure, or adjust the patient's toothbrush. For example, if the patient has sensitive gums, the professional may recommend the patient of the toothbrush for one minute instead of two minutes. In this case, the recommendations transmitted to the patient's toothbrush may configure the timer in the toothbrush to reflect one minute instead of two minutes. In another embodiment, the patient may configure the toothbrush based on the professional recommendations. This may allow the system described herein to be an interactive system between the patient and professional and, as a result, the patient and professional are more involved to monitor oral hygiene. By bringing the patient and professional closer in communication with each other, oral hygiene can be improved and can reduce other diseases evolving from bad oral hygiene.

Figure 13:
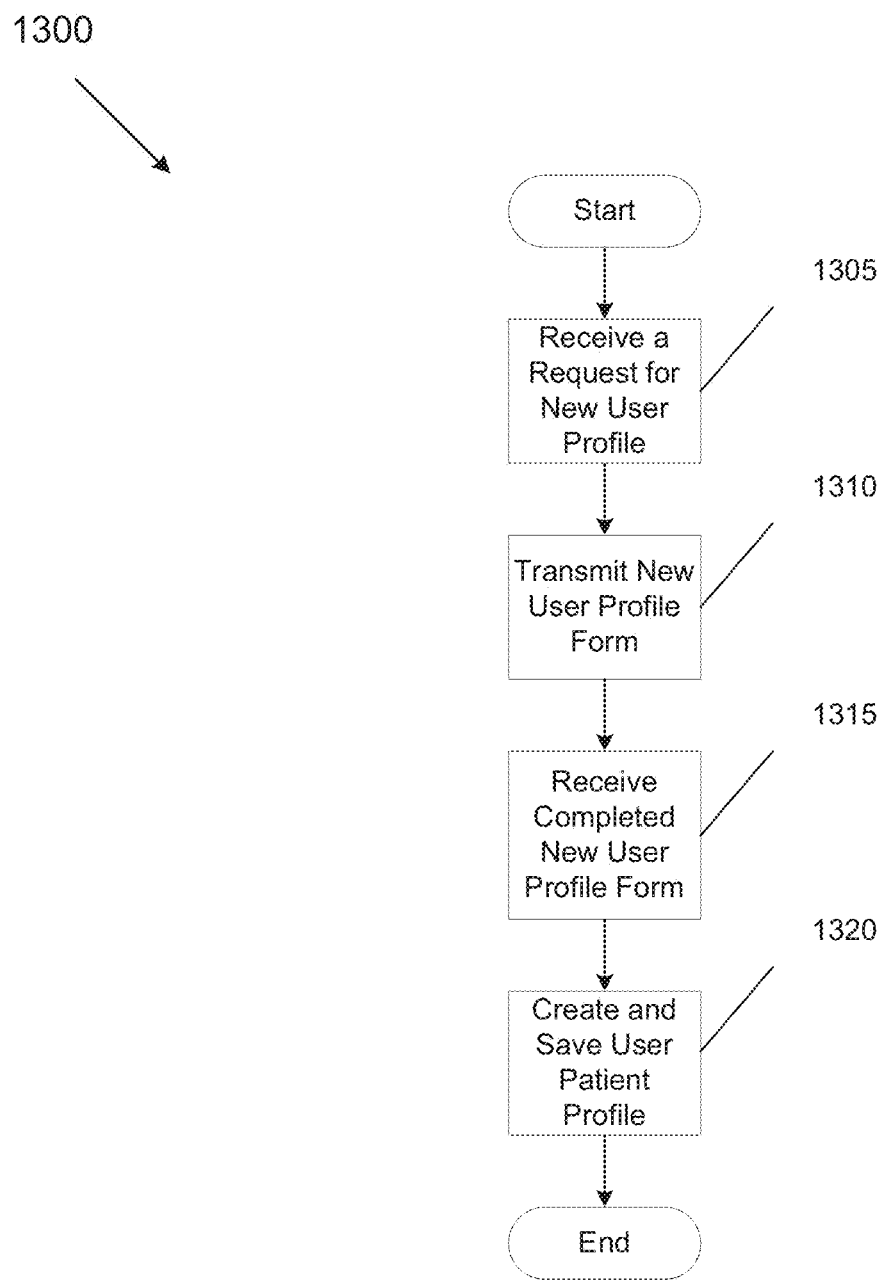
FIG. 13 is a flow diagram illustrating a process for creating a new user profile, according to an embodiment of the present invention.

FIG. 13 is a flow diagram illustrating a process 1300 for creating a new user profile, according to an embodiment of the present invention. In some embodiments, process 1300 may be executed by analytical module 830 of remote server 800. Process 1300 may begin with the remote server receiving a request at 1305 for creating a new user profile. The request may be received when the user accesses a webpage of the remote server and, in particular, a webpage that allows a user to create a user profile for a toothbrush.

At 1310, the remote server may transmit a new user profile form to a computing system of the user. This may allow the user to enter information into the new user profile form. Information that may be entered into the form may include, but is not limited to, the user name, age, sex, last dental visit, next scheduled dental visit, preferred professional, toothbrush information, the number of times the user brushes his or her teeth per day, etc. Toothbrush information may include, but is not limited to, the type of toothbrush used, the type of bristles, the type of toothpaste, etc. This embodiment may also allow the user to configure the toothbrush, i.e., with user-defined toothbrush configuration settings. For example, the user may define when brushing data should be uploaded to the remote server from the toothbrush.

At 1315, the remote server may receive a completed new user profile form from the computing system of the user, and, at 1320, the remote server may create and save a new user profile in the database of the remote server.

Figure 14:
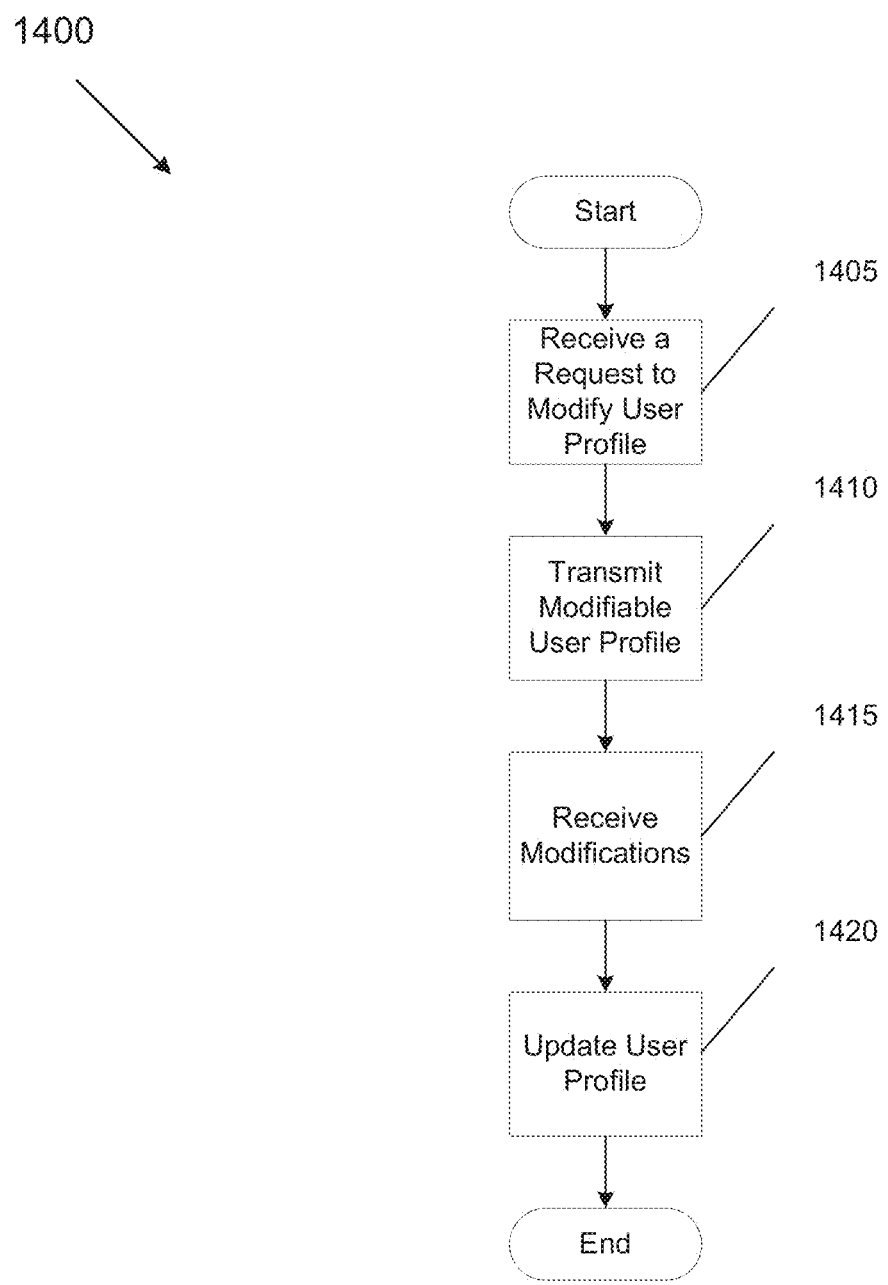
FIG. 14 is a flow diagram illustrating a process for modifying a user profile, according to an embodiment of the present invention.

FIG. 14 is a flow diagram illustrating a process 1400 for modifying a user profile, according to an embodiment of the present invention. In some embodiments, process 1400 may be executed by analytical module 830 of remote server 800. Process 1400 may begin with the remote server receiving a request at 1405 for modifying an existing user profile. For example, once the user logs into a system through a webpage application, a mobile application, etc., the user may request for the remote server to modify the profile of the user.

At 1410, the remote server may provide the computing system of the user with a modifiable user profile. This may be a webpage application, a mobile application, etc., that contains the user profile fields that can be modified by the user. In one embodiment, the user may modify information such as including a new preferred professional, toothbrush information, the number of times user brushes his or her teeth per day, the type of toothbrush used, the type of bristles, the type of toothpaste, etc. The user may also modify the user-defined toothbrush settings in certain embodiments. Once the updated information is inputted in the fields, the user may submit the modifications to the user profile, and the remote server may receive at 1415 the modifications to the user profile. At 1420, the remote server may update the user profile in a database of the remote server.

Figure 15A:
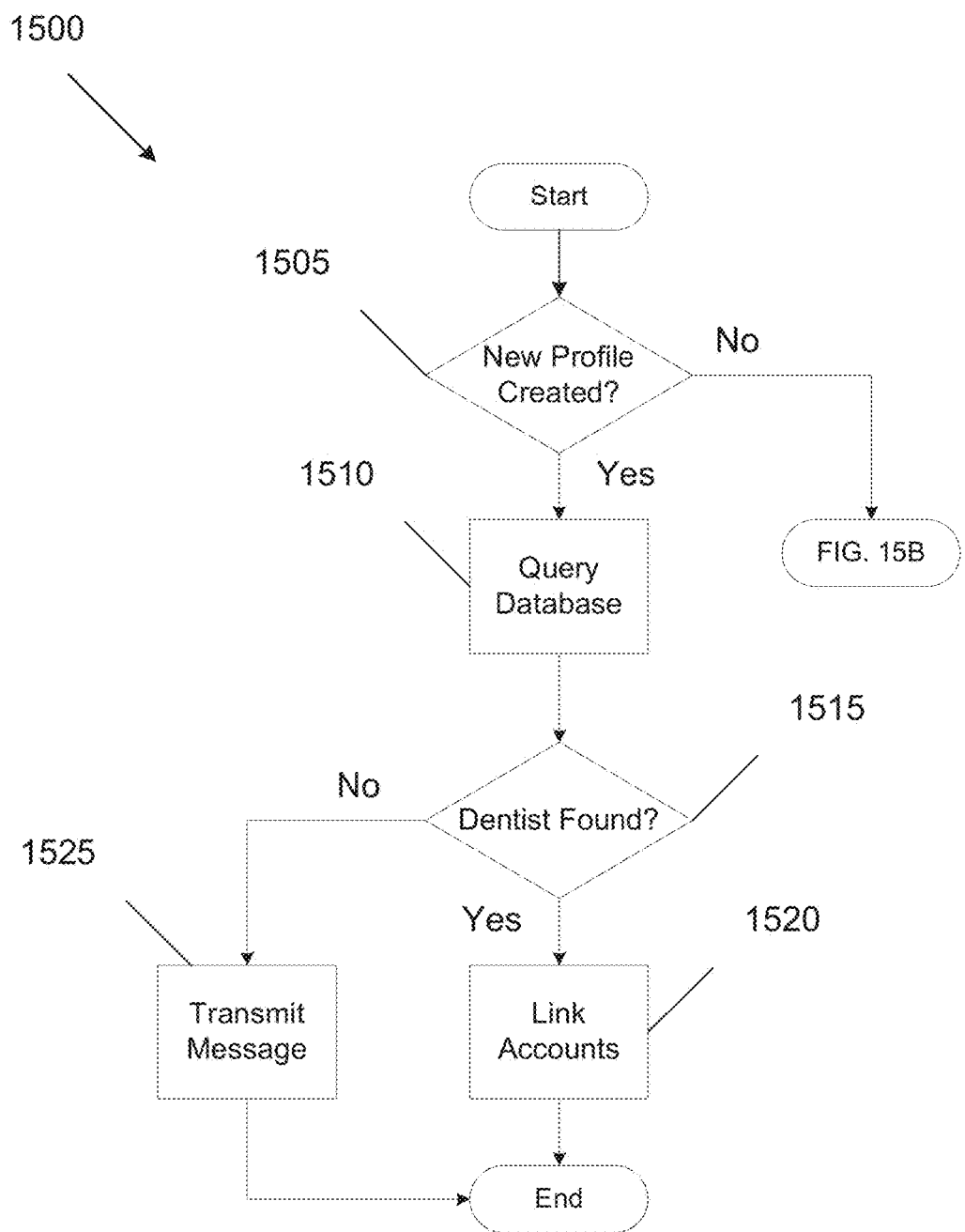

FIGS. 15A and 15B are flow diagrams illustrating a process 1500 for linking a professional when a new user profile is created or modified, according to an embodiment of the present invention. In some embodiments, process 1500 may be executed by analytical module 830 of remote server 800. Process 1500 begins with the remote server determining at 1505 whether a user has created a new user profile. If a new user profile has been created, the remote server may query at 1510 a database of registered professionals for the preferred professional listed in the new user profile. If the preferred professional is found at 1515, the remote server links at 1520 the preferred professional account with the user's account, such that the preferred professional may have access to the user's brushing habits when captured by the toothbrush. If the preferred professional is not found at 1515, the remote server transmits at 1525 a message to the computing device of the user to inform the user that the preferred professional is not connected with the system. This may allow the user to select another professional or ask the preferred professional to connect to the system.

Returning back to 1505, if the remote server determines the user has modified the user profile, the remote server determines at 1530 whether the user has updated the preferred professional field. If the user has not updated the preferred professional field, process 1500 terminates. If the user has updated the preferred professional field, the remote server queries at 1535 a database of registered professionals for the preferred professional listed in the updated/modified user profile. If the preferred professional is found at 1540, the remote server links at 1545 the preferred professional account with the user's account, such that the preferred professional may have access to the user's brushing habits when captured by the toothbrush. If the preferred professional is not found at 1540, the remote server transmits at 1550 a message to the computing device of the user to inform the user that the preferred professional is not connected with the system. This may allow the user to select another professional or ask the preferred professional to connect to the system.

Figure 16:
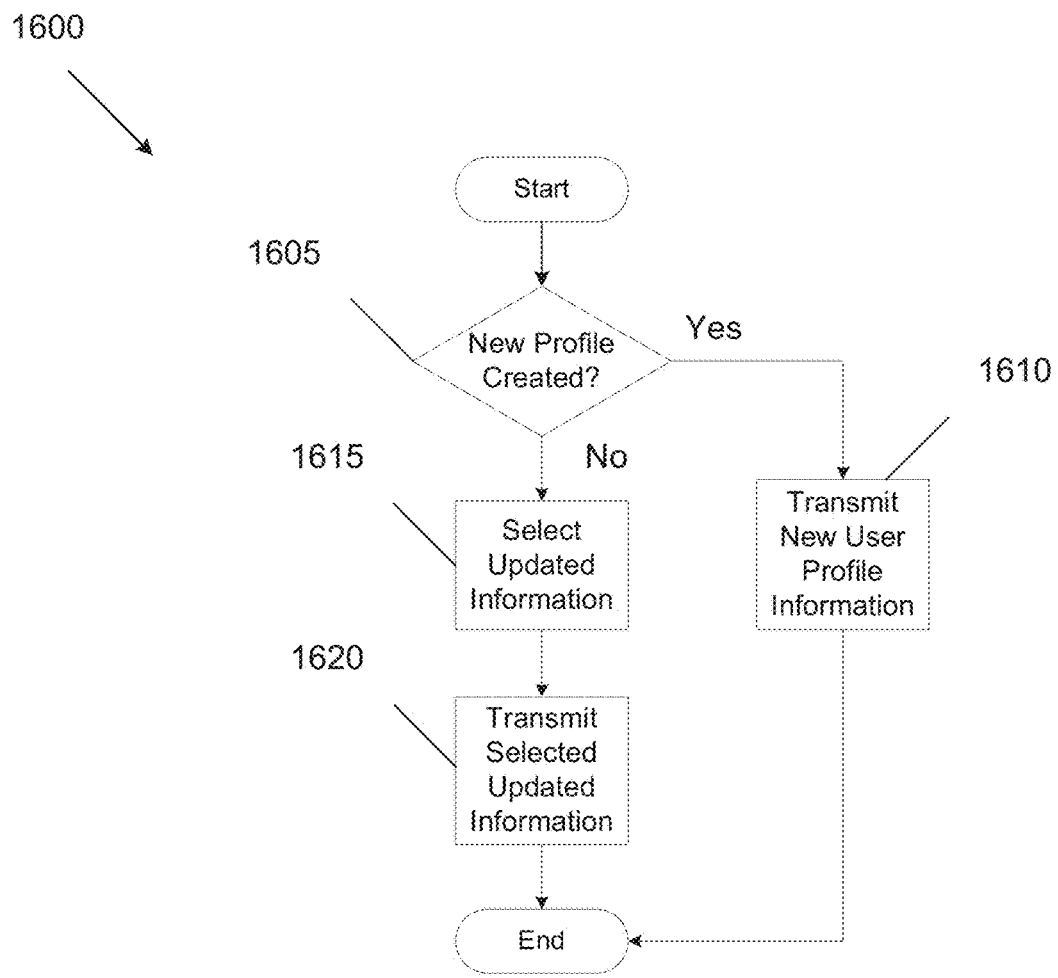
FIG. 16 is a flow diagram illustrating a process for synchronizing the toothbrush with a remote server when a new user profile is created or modified, according to an embodiment of the present invention.

FIG. 16 is a flow diagram illustrating a process 1600 for synchronizing the toothbrush with a remote server when a new user profile is created or modified, according to an embodiment of the present invention. In some embodiments, process 1600 may be executed by analytical module 830 of remote server 800. Process 1600 begins with the remote server determining whether a new user profile is created at 1605. If a new user profile is created, the remote server transmits at 1610 the new user profile, including user-defined toothbrush configuration settings, to the toothbrush. If the remote server determines that an existing user profile is updated, the remote server selects at 1615 the updated data in the user profile, along with updated user-defined toothbrush configuration settings. At 1620, the remote server transmits the selected updated data, along with the selected updated user-defined toothbrush configuration settings, to the toothbrush.

Figure 17:
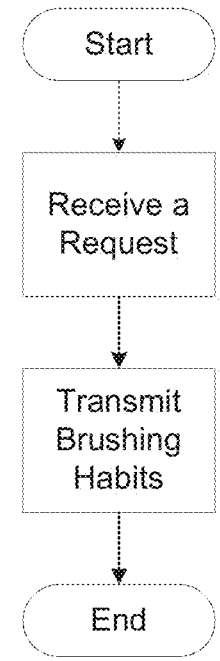
FIG. 17 is a flow diagram illustrating a process for viewing brushing habits, according to an embodiment of the present invention.

FIG. 17 is a flow diagram illustrating a process 1700 for viewing brushing habits, according to an embodiment of the present invention. In some embodiments, process 1700 may be executed by analytical module 830 of remote server 800. In this embodiment, process 1700 begins receiving a request at 1705 to view brushing habits from a computing device of a user. At 1710, the remote server transmits the brushing habits of the user to the computing device so the user can view his or her brushing habits. This may allow the user to view brush usage details over a predefined time period or over any time period depending on the configuration of the user profile.

In certain embodiments, the professional recommendations are also transmitted to the user. In other embodiments, the user may request professional recommendations from the remote server in order to view the professional recommendations.

Figure 18:
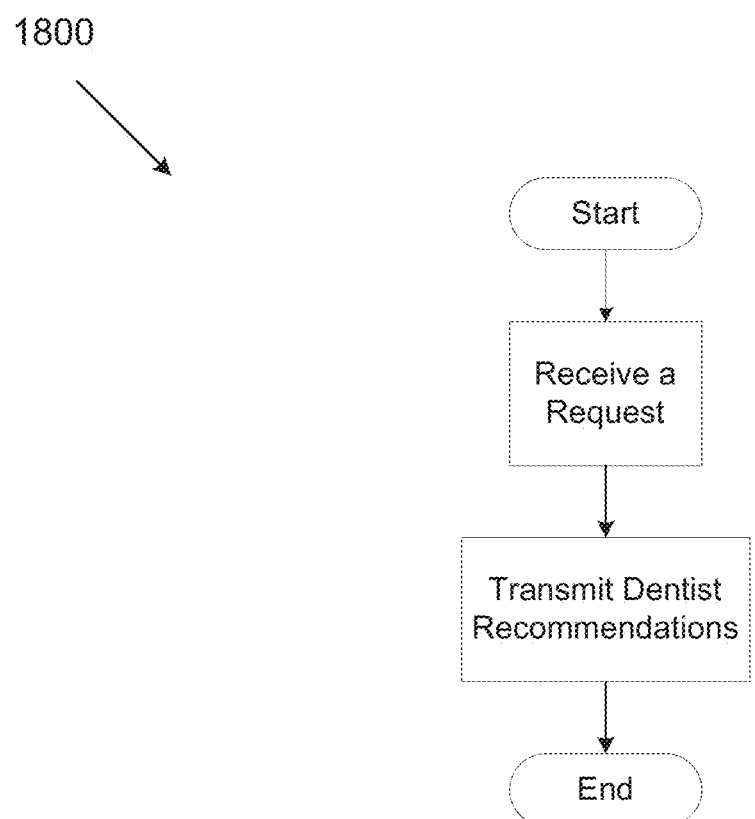
FIG. 18 is a flow diagram illustrating a process for viewing professional recommendations, according to an embodiment of the present invention.

FIG. 18 is a flow diagram illustrating a process 1800 for viewing professional recommendations, according to an embodiment of the present invention. In some embodiments, process 1800 may be executed by analytical module 830 of remote server 800. Process 1800 begins with the remote server receiving a request at 1805 from the computing device of the user to view professional recommendations. In response to the request, the remote server may transmit at 1810 the professional recommendations to the computing device of the user.

The method steps shown in FIGS. 3-7 and 9-18 may be performed, in part, by a computer program, encoding instructions for a nonlinear adaptive processor to cause at least the methods described in FIGS. 3-7 and 9-18 to be performed by the apparatuses discussed herein. The computer program may be embodied on a non-transitory computer readable medium. The computer readable medium may be, but is not limited to, a hard disk drive, a flash device, a random access memory, a tape, or any other such medium used to store data. The computer program may include encoded instructions for controlling the nonlinear adaptive processor to implement the methods described in FIGS. 3-7 and 9-18, which may also be stored on the computer readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an application specific integrated circuit ("ASIC").

Figure 19:
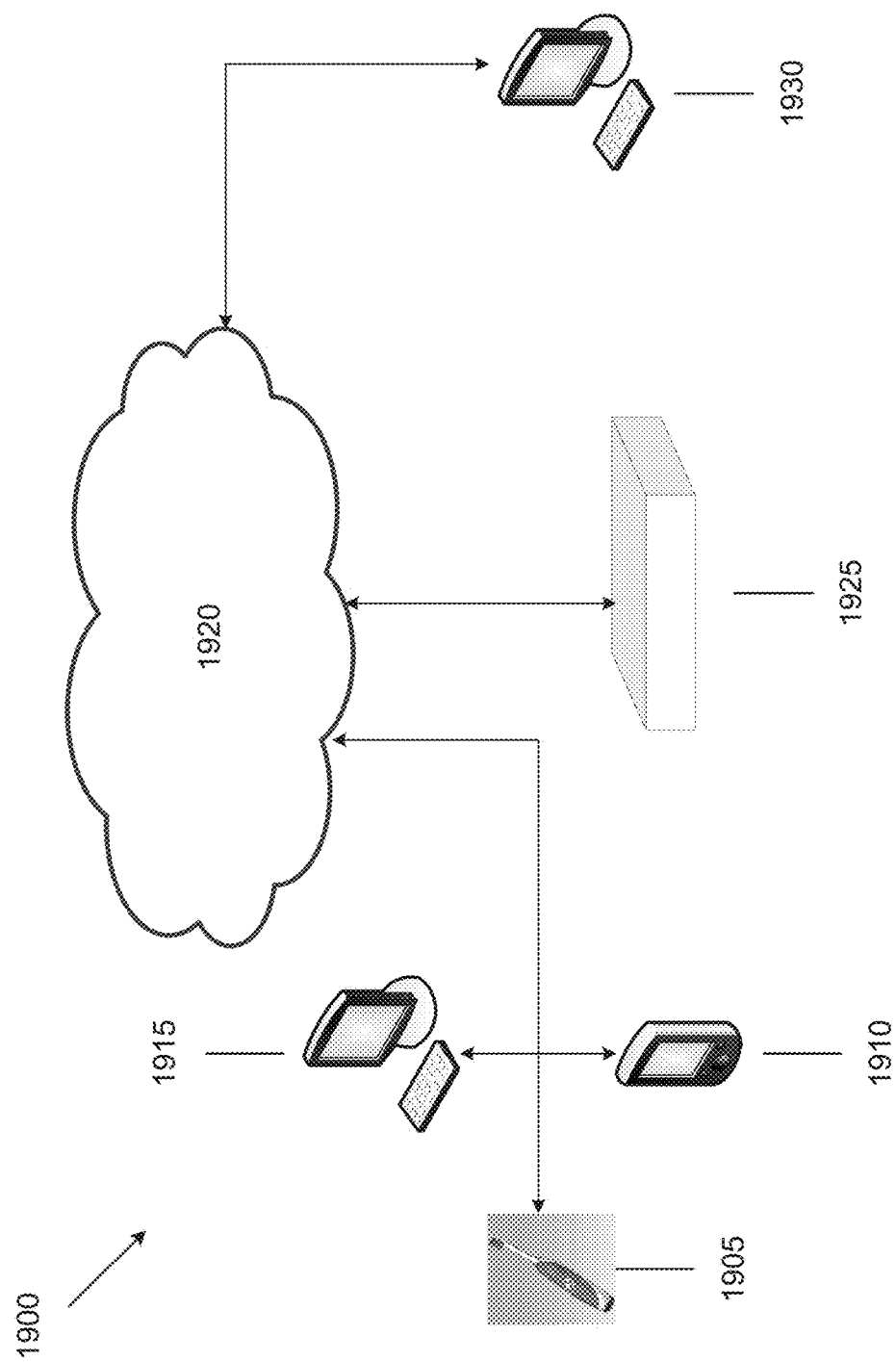
FIG. 19 is a diagram illustrating a system for capturing and sharing brushing data, according to an embodiment of the present invention.

FIG. 19 is a diagram illustrating a system 1900 for capturing and sharing brushing data, according to an embodiment of the present invention. In this embodiment, the sensors (not shown) capture brushing data when a user is brushing his or her teeth and the captured brushing data is stored in a database (not shown) of toothbrush 1905. Toothbrush 1905, depending on the configuration, may transmit the stored brushing data to a personal digital assistant (PDA) (or smart phone) 1910 or a computing device 1915 of the user, or a server 1925 via Bluetooth connection, Wi-Fi connection, or any wireless communication means. It should be appreciated that toothbrush 1905 may transmit the brushing data to any computing device that would be appreciated by a person of ordinary skill in the art.

When server 1925 receives the brushing data of the user, server 1925 stores the brushing data of the user in a database (not shown). Once stored, a professional, for example, may access the database of server 1925 to review the brushing data of the user. This may allow the professional to push or transmit professional recommendations for the particular user to computing system 1915, PDA 1910, or toothbrush 1905. Such a system allows a professional to specifically tailor recommendations for each particular user of the toothbrush based on the captured brushing habits of the user.

One or more embodiments described herein pertain to an apparatus configured to capture the brushing habits of a user. The captured brushing habits may be stored in the apparatus and/or be transmitted to a remote server allowing a professional to view the brushing habits of the user. This may allow the professional to provide recommendations to the patient such that the patient can improve his or her brushing habits.

It will be readily understood that the components of the invention, as generally described and illustrated in the figures herein, may be arranged and designed in a wide variety of different configurations. Thus, the detailed description of the embodiments is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with an embodiment may be included in at least one embodiment of the invention. Thus, appearances of the phrases "in certain embodiments," "in some embodiments," "in other embodiments," or other similar language, throughout this specification do not necessarily all refer to the same embodiment or group of embodiments, and the described features, structures, or characteristics may be combined in any suitable manner in one or more embodiments.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A system, comprising:
   a toothbrush, comprising:
   a liquid crystal display (LCD) connected to at least one processor and memory of the toothbrush, the LCD configured to display a list of radio stations for a user to select, a mode of operation option, an audio option, a settings option, and a default option, a selection unit configured to enable the user to select a radio station from the list of radio stations for the user to listen to while brushing his or her teeth, at least one sensor configured to capture brushing data of the user while the user is brushing his or her teeth, and a communication device configured to transmit the brushing data of the user to a remote server for storage in a database of the remote server; and a computing device of a professional configured to access the database to review the brushing data of the user and transmit recommendations to the toothbrush via the remote server, wherein the toothbrush is configured to receive the recommendations from the computing device of the professional via the communication unit, reconfigure a mode of operation of the toothbrush and a timer of the toothbrush via a processor, and enable the user to view the recommendations via the LCD, and when the user selects a radio station from the list of radio stations using the selection unit, the toothbrush is configured to activate the selected radio station for a predetermined time period.

2. The system of claim 1, wherein the at least one sensor comprises an activation delay allowing the user time to place the toothbrush in his or her mouth before activating the sensor.

3. The system of claim 2, wherein the at least one sensor is deactivated after a predefined period of time has elapsed or after the user discontinues brushing his or her teeth.

4. The system of claim 1, wherein the at least one sensor is located in the brushing head of the toothbrush to capture brushing motion, pressure applied to teeth, and quadrants brushed.

5. The system of claim 1, wherein the brushing data of the user is deleted from the toothbrush after the communication device transmits the brushing data of the user.

6. The system of claim 1, wherein the remote server is configured to evaluate the brushing data of the user to determine brushing habits of the user.

7. The system of claim 1, wherein the toothbrush is configured to receive an update message from the computing system via the remote server, the update message automatically adjusts settings of the toothbrush.

8. The system of claim 1, wherein the remote server is configured to user defined toothbrush settings from a client device of the user, and transmit the user defined toothbrush settings to the toothbrush.

9. The system of claim 8, wherein the toothbrush is configured to update settings based on the user defined toothbrush settings.

* * * * *